(12) United States Patent
Tokumura et al.

(10) Patent No.: US 6,239,115 B1
(45) Date of Patent: May 29, 2001

(54) DRY FLOWABLE POLYOXIN COMPOSITIONS

(75) Inventors: Jun Tokumura, Tokyo; Shinichiro Kochi, Shizuoka; Tomoki Yoshimura, Tokyo, all of (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/192,331

(22) Filed: Nov. 16, 1998

(30) Foreign Application Priority Data

Nov. 17, 1997 (JP) .................................................... 9-332499

(51) Int. Cl.[7] ............................ A61K 31/70; A01N 43/04
(52) U.S. Cl. ............................. 514/43; 514/25; 424/116; 424/709; 424/710
(58) Field of Search ................................... 424/116, 709, 424/710; 514/25, 43

(56) References Cited

U.S. PATENT DOCUMENTS 4,007,267 * 2/1977 Kishi et al. .
6,051,533 * 4/2000 Kajikawa et al. .

FOREIGN PATENT DOCUMENTS 48-1510B 1/1973 (JP) .
61-236701A 10/1986 (JP) .

* cited by examiner

*Primary Examiner*—James O. Wilson
(74) *Attorney, Agent, or Firm*—Nixon & Vanderhye

(57) ABSTRACT

Disclosed are dry flowables containing polyoxin compound, surfactant and water-soluble inorganic material. The dry flowables of the present invention have good friability, dispersibility and suspensibility when mixed with water, and have an excellent characteristic that they can efficiently bring out the activity of polyoxin compounds as agricultural chemicals.

16 Claims, No Drawings

DRY FLOWABLE POLYOXIN COMPOSITIONS

BACKGROUND OF THE INVENTION

1. Field of the Invention

The present invention relates to a dry flowable for plant disease control containing a polyoxin compound.

2. Related Art

Polyoxin compounds produced by *Streptomyces cacaoi* var. asoensis are nucleoside antibiotics, and they have been known to inhibit growth of pathogenic fungus of plant diseases such as rice sheath blight, pear Alternalia leaf spot, and rice brown spot. Therefore, agricultural chemicals containing the polyoxin compounds as an active ingredient in the form of emulsifiable concentrate and wettable powders have been marketed, and they have been used as fungicide for fruit orchards, tobacco, flowers, turfgrass and the like for the past 30 years or more.

However, the conventional emulsifiable concentrate containing the polyoxin compounds have a drawback that they are unstable as emulsions, and hence suffer from a short effective self-life. Therefore, their use may be limited, and aged emulsions must be discarded. In addition, activity of such conventional emulsifiable concent is not always stable depending on the kind of solvent used, diluted concentration and the like, and therefore they are not always convenient for use.

On the other hand, conventional wettable powders containing the polyoxin compounds also have drawbacks, for example, low content of active ingredient, dusty, unstable friability and dispersibility. Further, because they use clay minerals as a carrier, such clay minerals may adhere to plants to form noticeable taints.

As described above, the conventional formulations containing the polyoxin compounds have various kinds of problems, and there has been a need for developing a novel formulation which overcomes the problems mentioned above.

Meanwhile, environmental pollution due to excessive use of agricultural chemicals has recently become to be paid much attention as a social problem. That is, it is required to prevent as far as possible agricultural chemicals applied to plants or soil from flowing out to neighboring rivers with rainwater and the like to affect on fish occurring in the rivers, to contaminate source for water supply and the like. Therefore, it is desired to provide agricultural chemicals exhibiting excellent activity with a small amount. In particular, such chemicals are highly desirable for golf courses where total amount of agricultural chemicals to be used is limited by regulations.

Further, there are some diseases among those of turfgrass in golf courses and the like for which sufficient activity cannot be obtained unless a locally increased application amount of agricultural chemicals is used. Because the conventional wettable powders do not have sufficient friability, dispersibility and susupensibility, and they have a low content of active ingredients, a lot of water must be used for applying such formulations. Therefore, when such conventional wettable powders are used, greens in golf courses may be drowned and this may make it difficult to play golf. Therefore, there is also a need for developing a formulation requiring less water for application.

An object of the present invention is to solve these problems observed in the prior art. That is, the object of the present invention is to provide a dry flowable containing a polyoxin compound having good friability, dispersibility and suspensibility when mixed with water. Another object of the present invention is to provide a dry flowable capable of efficiently bring out the activity of polyoxin compounds as agricultural chemicals, having a high content of active ingredient, and requiring less amount of water for application.

SUMMARY OF THE INVENTION

In order to achieve the objects mentioned above, the present inventors conducted various studies. As a result, they have found that a dry flowable prepared by mixing a polyoxin compound with a surfactant and a water-soluble inorganic material can efficiently bring out the plant disease control effect of the polyoxin compound, and thus completed the present invention.

Therefore, the present invention provides a dry flowable containing a polyoxin compound, a surfactant and a water-soluble inorganic material.

The dry flowable of the present invention preferably contains at least one polyoxin compound produced by *Streptomyces cacaoi* var. asoensis as the polyoxin compound. The dry flowable of the present invention also preferably contains as the polyoxin compound one or more compounds selected from the group consisting of polyoxin A, polyoxin B, polyoxin D, polyoxin E, polyoxin F, polyoxin G, polyoxin H, polyoxin J, polyoxin K, polyoxin L, polyoxin M, polyoxin N, polyoxin O and salts thereof. Polyoxin B and polyoxin D are preferred among these, and the salts are preferably zinc salts, iron salts or titanium salts. Particularly preferred is zinc salt of polyoxin D. The dry flowable of the present invention preferably contains a polyoxin compound in an amount of 5–30% by weight.

The dry flowable of the present invention preferably contains, as the surfactant, an anionic surfactant such as formalin condensates of sodium naphthalenesulfonate, or a nonionic surfactant such as polyoxyethylene alkyl ethers. As the water-soluble inorganic material, it can contain, for example, sodium sulfate or ammonium sulfate. It is preferred that the dry flowable of the present invention have a particle size in the range of 90–500 $\mu$m, more preferably in the range of 90–355 $\mu$m.

The dry flowable of the present invention can be used for the prevention or the therapy cf, for example, large patch, brown patch, Rhizoctonia patch, Helminthosporium leaf blight, Curvularia leaf blight, and fairy rings of turfgrass, powdery mildew of rose plants and the like. For large patch, brown patch, Rhizoctonia patch, Helminthosporium leaf blight, Curvularia leaf blight, and fairy rings of turfgrass, the dry flowable of the present invention is preferably applied at early stage or before dormant period of these diseases. The dry flowable of the present invention can be mixed with water, and applied to plants or soil.

The dry flowable of the present invention can be produced, for example, by spraying a surfactant into a fluidized bed containing a polyoxin compound and a water-soluble inorganic material, granulating the bed with drying, and selecting particles having a particle size within the range of 90–500 $\mu$m. It can also be produced by granulating a mixture containing a polyoxin compound, a surfactant and a water-soluble inorganic material by manual extrusion through a screen, drying the extruded particles, and selecting particles having a particle size within the range of 90–500 $\mu$m.

DESCRIPTION OF THE PREFERRED EMBODIMENTS

The dry flowable of the present invention will be explained in detail hereinafter.

The dry flowable of the present invention contains a polyoxin compound, a surfactant and a water-soluble inorganic material as essential ingredients.

The polyoxin compound is added to the dryflowable of the present invention as an active ingredient of agricultural chemicals. Preferred examples of the polyoxin compound include, for example, polyoxin A, polyoxin B, polyoxin D, polyoxin E, polyoxin F, polyoxin G, polyoxin H, polyoxin J, polyoxin K, polyoxin L, polyoxin M, polyoxin N, polyoxin O and salts thereof. While the kind of the salts are not particularly limited, preferred are zinc salts, iron salts and titanium salts. These polyoxin compounds may be used alone, or in any combination of two or more kinds of them. Among these, preferred are polyoxinB, polyoxin Dandsalts thereof, and more preferred are polyoxin D and salts thereof. It is particularly preferred to use zinc salt of polyoxin D (Japanese Patent Publication (KOKOKU) No. (Sho) 46-13364/1971). The chemical structures of major polyoxin compounds are mentioned in "THE MERCK INDEX TWELFTH EDITION", page 1306.

The polyoxin compound used for the dry flowable of the present invention may be either one provided by a fermentation process, or one provided by chemical synthesis. When one obtained by a fermentation process is used, for example, those polyoxin compounds produced by *Streptomyces cacaoi* var. asoensis can be used. Conditions and methods for its cultivation may be suitably selected depending on the kind and/or amount of a polyoxin compound to be obtained. The product of *Streptomyces cacaoi* var. asoensis may be used after purification, or may be used as a crude product.

For the dry flowable of the present invention containing a polyoxin compound, various surfactants generally used for the production of dry flowables can be used. However, it preferably contains inter alia an anionic surfactant or a nonionic surfactant, and more preferably contains both of them.

Examples of the anionic surfactant include, for example, formalin condensates of naphthalenesulfonic acid salts, alkenylsulfonic acid salts, alkylnaphthalenesulfonic acid salts, ligninsulfonic acid salts, alkylallylsulfonic acid salts, polystyrenesulfonic acid salts, carboxymethylcellulose salts and the like. Examples of the salts include, for example, alkali metal salts such as sodium salts and alkaline earth metal salts such as calcium salts. These anionic surfactants may be used alone or in any combination of two or more of them. Among these, formalin condensates of naphthalenesulfonic acid salts are preferably used, and formalin condensates of sodium naphthalenesulfonate is particularly preferably used.

Examples of the nonionic surfactant include, for example, polyoxyethylene alkyl ethers, polyoxyethylene dialkyl ethers, polyoxyethylene alkyl aryl ethers, polyoxyethylene dialkyl aryl ethers, polyoxyethylene stylyl aryl ethers, polyoxyethylene distylyl aryl ethers, polyoxypropylene alkyl ethers, polyoxypropylene dialkyl ethers, polyoxypropylene alkyl aryl ethers, polyoxypropylene dialkyl aryl ethers, polyoxypropylene stylyl aryl ethers, polyoxypropylene distylyl aryl ethers, polyoxyethylene polyoxypropylene ethers, polyoxyethylene alkyl esters, polyoxyethylene sorbitan fatty acid esters, polyoxypropylene alkyl esters, polyoxypropylene sorbitan fatty acid esters, sorbitan fatty acid esters, polyoxyethylene polyoxypropylene block polymers, higher fatty acid alkanolamides and the like. These nonionic surfactants may be used alone or in any combination of two or more of them. Among these, polyoxyethylene alkyl ethers are particularly preferably used.

The dry flowable of the present invention also contains a water-soluble inorganic material as an essential ingredient.

The water-soluble inorganic material to be used is preferably selected from those not unduly deteriorating the granulation property of the dry flowable of the present invention. As the water-soluble inorganic material, either one kind of the material or any combination of two or more kinds of the material may be used. As the water-soluble inorganic material, sodium sulfate or ammonium sulfate may be preferably used, and ammonium sulfate is particularly preferably used.

The dry flowable of the present invention may contain, in addition to the polyoxin compound, the surfactant, and the water-soluble inorganic material, other ingredients in an amount not unduly deteriorating the advantage of the present invention.

For example, solid carriers commonly used for usual wettable powders can be used. Specifically, clay minerals such as bentonite, kaolinite, montmorillonite, and zirkelite can be used. As anextender or the like, talc, mica, soda lime, apatite, diatomaceous earth, magnesium carbonate, silicic anhydride, pumice, vermiculite, gypsum, calcium carbonate, dolomite, zeolite, dextrin, sodium salts of carboxymethylcellulose, polyvinylpyrrolidone, sodium polyacrylate, polyvinyl alcohol, sodium ligninsulfonate, starch, crystalline cellulose, urea, wax and the like can be used. These additives are used in such an amount that friability, dispersibility and suspensibility of the dry flowable of the present invention should not be unduly deteriorated.

The dry flowable of the present invention may also contain, as an active ingredient of agricultural chemicals, insecticides, acaricides, herbicides, fungicides, plant growth regulators, synergists and the like. However, amount of these agents should be in such a range that the activity of polyoxin compound should not be unduly deteriorated.

The composition of the ingredients of the dry flowable of the present invention is not particularly limited so long as the intended purpose of the present invention can be achieved. However, the dry flowable preferably contains 5–30% by weight of the polyoxin compound. As for the amounts of the other ingredients, 1–3 parts by weight of the nonionic surfactant, 0.1–0.3 parts byweight of the anionic surfactant, and 1–5 parts by weight of the water-soluble inorganic material can be preferably used with 1 part by weight of the polyoxin compound.

The method for producing the dry flowable of the present invention is not particularly limited, and methods commonly used for the manufacture of usual dry flowables can be utilized. For example, the dry flowable can be prepared by granulation based on spray-drying, tumbling granulation, fluidized bed granulation, mixing granulation by agitation, extrusion granulation, grinding granulation or the like, and drying the resulting granules. When the production is performed by the fluidized bed granulation, it is preferred that a fluidized bed containing a polyoxin compound, surfactant and water-soluble inorganic material is granulated while being dried. It is particularly preferred that a surfactant is sprayed into a fluidized bed containing a polyoxin compound and a water-soluble inorganic material, and the fluidized bed is granulated under drying. Alternatively, the dry flowable can also be prepared by granulating a mixture containing a polyoxin compound, surfactant and water-soluble inorganic material by manual extrusion through a screen, and drying the extruded particles.

When granules are sieved, granules within the desired particle size range can be obtained by suitably adjusting mesh size of a sieve. The particle size of the dry flowable of the present invention is preferably in the range of 90–500 µm, more preferably in the range of 90–355 µm. The dry flowable of the present invention is also referred to as water dispersible granule.

The dry flowable of the present invention is characterized in that it is extremely excellent in physical properties when mixed with water. That is, when the dry flowable of the present invention is added to water, it immediately begins to friableness, and disperse quickly. Because of such high friability and dispersibility, the ingredients are sufficiently dispersed when the dry flowable of the present invention is mixed with water before application, and a dispersion for application can be prepared quickly. Accordingly, by using the dry flowable of the present invention, it becomes possible to obtain excellent control effect even if it is applied immediately after mixing with water, and thereby time and cost can be saved.

The dry flowable of the present invention is also characterized in that the ingredients dispersed in water are not precipitated but suspended in the water for a relatively long time. Because of this extremely high suspensibility, it is possible to obtain sufficient control effect even if time for stirring before the application is shortened or the stirring is omitted. That is, the dry flowable of the present invention also has an advantage that it is also effective for the case where the time from mixing with water to application is relatively long.

The dry flowable of the present invention is further characterized in that it requires a less amount of water for dilution because it has a higher content of the active ingredient compared with conventional wettable powders. The less amount of water required for dilution enables formation of agricultural chemical having a high concentration, which can bring out the control effect more efficiently. Therefore, by using the dry flowable of the present invention, the amount of water for application can be reduced, which is advantageous for application where the amount of water for application should be reduced. In particular, the dry flowable of the present invention is advantageous for greens of golf courses, because drowned green may hamper playing golf. In addition, use of the dry flowable of the present invention eliminate the need for application of excessive amount of the agricultural chemical, and hence environmental pollution can be stanched.

The dry flowable of the present invention can also prevent taints of plants. Clay minerals frequently used in conventional agricultural chemicals adhere to surfaces of plants when applied, and generally remain there for a long period of time. Such clay minerals adhered to surfaces of plants may be noticeable as taints, and therefore may greatly reduce the value of the plants, especially when houseplants are cultivated. When crop plants are cultivated, appearance of harvest may be deteriorated, and hence the commercial value of the harvest is reduced. Because the dry flowable of the present invention does not contain any clay minerals, such drawbacks as mentioned above can be eliminated by controlling the amount of clay minerals to be used depending on the kind of objective plants.

The dry flowable of the present invention can be used to effectively control various plant diseases to which emulsifiable concentrate or wettable powders have conventionally been applied to control them. The kind of plant diseases to be controlled is not particularly limited.

It has been confirmed that the dry flowable of the present invention shows higher fungicidal activity against, in particular, large patch, brown patch, Rhizoctonia patch, Helminthosporium leaf blight, Curvularia leaf blight, and fairy rings of turfgrass, and powdery mildew of rose plants compared with conventional wettable powders.

The method for applying the dry flowable of the present invention to plants or soil is not particularly limited. It is usually mixed with water and sprayed on plants. The mixing ratio with water is generally in such a range that the concentration of the active ingredient as agricultural chemical, the polyoxin compound, should be 20–400 ppm. However, for controlling powdery mildew of rose plants, 500 to 6000-fold dilution of the dry flowable of the present invention is generally used. When it is mixed with water, other agents such as insecticides, acaricides, herbicides, fungicide, plant growth regulators, and synergists can be mixed.

The application amount of the dry flowable of the present invention is suitably selected considering application situation, application time, application method, object of control and the like. For example, when a dry flowable containing zinc salt of polyoxin D is used, it is suitably used in an amount of 0.25–2.5 $g/m^2$ per one application for controlling large patch, brown patch, Rhizoctonia patch, Helminthosporium leaf blight, and Curvularia leaf blight of turfgrass, or 30–60 $g/m^2$ per one application for controlling fairy rings.

The method for application may be, for example, spraying by a sprayer. As the objective portion of plants, for example, stalks and leaves of plants, soil and the like may suitably be selected depending on the kind of the disease to be controlled. The application location may be, for example, rice paddy, field, orchard, golf course and park having turfgrass, meadow, forest, plateau, potted plant and the like.

The dry flowable of the present invention may be applied before onset of plant disease for prevention, or after onset of plant disease for control. In particular, the objective disease is a disease of turfgrass, it may also be effective for control after onset of the disease. Application before infection or at early stage of infection may be effective for large patch, brown patch, Helminthosporium leaf blight, and Curvularia leaf blight. Application before dormancy may be the most effective for Rhizoctonia patch.

As described above, the dry flowable of the present invention containing a polyoxin compound has good friability, dispersibility and suspensibility when mixed with water. Further, according to the present invention, a dry flowable having a high content of active ingredient can be produced, which can efficiently manifest the agricultural chemical activity of the polyoxin compound. Therefore, the dry flowable of the present invention can much reduce the amount of water required for applying the polyoxin compound. Furthermore, because the dry flowable of the present invention does not show dusty, and is excellent in storage stability, its handling is easy. Moreover, because the dry-flowable of the present invention does not contain clay minerals as an essential ingredient, it can be formulated so as not to taint plants to which the dry flowable should be applied.

Because of these excellent characteristics of the dry flowable of the present invention, it can be widely utilized for various cases requiring the disease control by the polyoxin compound. In particular, it can be effectively used for when the amount of agricultural chemicals to be used should be restrained, when the amount of application is desired to be reduced, when prevention of environmental pollution is regarded and the like.

The present invention will be further explained more specifically with reference to the following preparation examples and test examples. The materials, amounts, compositions, procedures and the like used in the following examples may be suitably modified within the scope of the present invention. Therefore, the present invention should not be construed to be limited by the following specific examples.

The expressions of "%" and "part(s)" mentioned hereinafter mean % by weight and part(s) by weight unless otherwise indicated. The bulk product of zinc salt of polyoxin D used for the manufacture of dry flowables was a bulk product containing zinc salt of polyoxin D at a purity of 22%.

EXAMPLE 1

Fifty parts of polyoxin D zinc salt bulk product and 30 parts of ammonium sulfate were placed in a fluidized bed granulator to form a fluidized bed, which was mixed sufficiently while sprayed with 2 parts of polyoxyethylene alkyl ether. The fluidized bed was further sprayed with 18 parts of formalin condensate of sodium naphthalenesulfonate as a 40% aqueous solution, and granulated with drying at 50–60° C. Then, the resulting particles were classified according to the specified particle size with a vibrating screen separator to afford dry flowable containing 11% of zinc salt of polyoxin D having a particle size of 250–500 μim.

EXAMPLE 2

By repeating the same procedure as in Example 1 except that the sieve was changed, dry flowable containing 11 of zinc salt of polyoxin D having a particle size of 90–355 μm was obtained.

EXAMPLE 3

Fifty parts of polyoxin D zinc salt bulk product, 30parts of ammonium sulfate, 18 parts of formalin condensate of sodium naphthalenesulfonate, and 2 parts of polyoxyethylene alkyl ether were placed in a beaker so that the total weight of the materials should be 500 g, and mixed sufficiently. Then, 200 ml of water was gradually added to the mixture, and the mixture was kneaded and granulated by manual extrusion through a 0.7 mm screen. The resulting particles were dried at 60° C. and classified with a sieve to afford dry flowable containing 11% of zinc salt of polyoxin D having a particle size of 250–500 μm.

EXAMPLE 4

Fifty parts of polyoxin D zinc salt bulk product, 30 parts of ammonium sulfate, and 20 parts of formalin condensate of sodium naphthalenesulfonate were placed in a beaker so that the total weight of the materials should be 500 g, and mixed sufficiently. Then, 220 ml of water was gradually added to the mixture, and the mixture was kneaded and granulated by manual extrusion through a 0.7 mm screen. The resulting particles were dried at 60° C., and classified with a sieve to afford dry flowable containing 11% of zinc salt of polyoxin D having a particle size of 250–500 μm.

EXAMPLE 5

Fifty parts of polyoxin D zinc salt bulk product, 15 parts of clay, 15 parts of ammonium sulfate, 18 parts of formalin condensate of sodium naphthalenesulfonate and 2 parts of polyoxyethylene alkyl phenyl ether sulfate were placed in a beaker so that the total weight of the materials should be 500 g, and mixed sufficiently. Then, 220 ml of water was gradually added to the mixture, and the mixture was kneaded and granulated by manual extrusion through a 0.7 mm screen. The resulting particles were dried at 60° C., and classified with a sieve to afford dry flowable containing 11% of zinc salt of polyoxin D having a particle size of 250–500 μm.

TEST EXAMPLE 1

Granulation property test

Granulation condition of the polyoxin dry flowables produced in Examples 1 and 3–5 was observed with the naked eye, and graded with the following three grades: "good", "acceptable" and "not acceptable".

TEST EXAMPLE 2

Friability test in water (1)

0.5 g each of the polyoxin dry flowables produced in Examples 1 and 3–5 was put into 100 ml of water in a 250 ml-volume cylinder, and its friability in water was observed and graded with the following three grades.

A: Most of particles are friabled until they reach the bottom of the cylinder.
B: Particles are dispersed in water with threading, or about 50% are friabled until they reach the bottom of the cylinder.
C: Most of particles are not friabled, and reach the bottom of the cylinder.

TEST EXAMPLE 3

Friability test in water (2)

0.5 g each of the polyoxin dry flowables produced in Examples 1 and 3–5 was put in 100 ml of water in a 250 ml-volume cylinder. The cylinder was slowly inverted 1 minute after the particles reached to the bottom of the cylinder, and the friability was examined. When all of the particles were not friabled, the procedure of slowly inverting the cylinder 2 seconds after the particles reached to the bottom of the cylinder was repeated until all of the particles of the polyoxin dry flowable were friabled. Number of inversion was recorded for each polyoxin dry flowable.

TEST EXAMPLE 4

Suspensibility test

After the friability in water was observed in Test Example 3, the cylinder was further inverted 20 times. Then, the dispersion was immediately transferred into a test tube, and the amount of precipitates were measured after 5, 15, and 30 minutes. The results of the aforementioned Test Examples 1–4 are shown in Table 1.

TABLE 1

| | Test Example 1 Granulation property | Test Example 2 friability in water (1) | Test Example 3 friability in water (2) | Test Example 4 Suspensibility (ml) | | |
|---|---|---|---|---|---|---|
| | | | | 5 minutes later | 15 minutes later | 30 minutes later |
| Example 1 | Good | B-A | 1 | 0.01 | 0.06 | 0.14 |
| Example 3 | Good | C-B | 2 | 0.02 | 0.05 | 0.08 |
| Example 4 | Good | C-B | 3 | 0.10 | 0.16 | 0.22 |
| Example 5 | Good | B-C | 7 | 0.14 | 0.18 | 0.20 |

In Test Example 2, evaluation "B-C" indicates higher friability in water than "C-B".

The results of Table 1 indicate that all of the dry flowables of the examples were excellent in the granulation property, friability in water, and suspensibility. In particular, the dry flowables of Example 1 and Example 3 were extremely excellent in these physical properties.

TEST EXAMPLE 5
Effect for brown patch of turfgrass

Comparative test of effect against brown patch of turfgrass was performed by using the polyoxin dry flowable of Example 2, a commercially available polyoxin wettable powder (trade name: Polyoxin Z Wettable Powder, active ingredient: 2.25% of zinc salt of polyoxin D, manufacturer: Kaken Pharmaceutical Co., Ltd., represented as "Comparative Example 1" hereinafter) and a mepronyl wettable powder (trade name: Clean Grass Wettable Powder, active ingredient: 75% of mepronyl, manufacturer: Riken Green Co., Ltd., represented as "Comparative Example 2" hereinafter).

Each agent was diluted in the predetermined degree of dilution shown in Table 2, and applied by a applicator for horticulture in an amount of 1 liter/m$^2$ to turfgrass (Pencross bentgrass) which showed brown patch on many spots. Application was performed every 12 days four times in total. The test was carried out in a plot of 1 m$^2$ for each test in duplicate. After the fourth application, proportion of lesion was determined for each plot. The results are shown in Table 2. Phytotoxicity was not seen in any plot when observed with the naked eye.

TABLE 2

| Tested Agent | Dilution | Active ingredient (%) | Proportion of lesion (%) |
| --- | --- | --- | --- |
| Example 2 | × 1000 | 0.0110 | 18.3 |
|  | × 2000 | 0.0055 | 20.4 |
| Comparative Example 1 | × 250 | 0.0090 | 34.8 |
|  | × 500 | 0.0045 | 38.5 |
| Comparative Example 2 | × 500 | 1.5 | 43.6 |
| No treatment |  |  | 64.2 |

The results of Table 2 indicate that the proportion of lesion of brown patch of turfgrass observed when the polyoxin dry flowable of Example 2 was applied was lower than those observed when the polyoxin wettable powder of Comparative Example 1 and the mepronyl wettable powder of Comparative Example 2 were applied. In particular, the polyoxin dry flowable of Example 2 exhibited distinctly higher activity compared with the mepronyl wettable powder of Comparative Example 2, and effectively restrained expansion of the brown patch at early stage.

TEST EXAMPLE 6
Effect for large patch of turfgrass Comparative test of effect against large patch of turfgrass was performed by using the polyoxin dry flowable of Example 2, a commercially available polyoxin wettable powder of Comparative Example 1, and a pencycuron wettable powder (trade name: Monceren Wettable Powder, active ingredient: 75% of pencycuron, manufacturer: Nihon Bayer Agrochem K.K., represented as "Comparative Example 3" hereinafter).

Each agent was diluted in the predetermined degree of dilution shown in Table 3, and applied by a power sprayer in an amount of 1 liter/m$^2$ to turfgrass (Japanese lawngrass [Noshiba], Zoysia japonica Steud.) which showed large patch on many spots. The agent was applied every 12 days four times in total. The test was carried out in a plot of 1 m$^2$ for each test in duplicate. After the fourth application, proportion of lesion was determined for each plot. The results are shown in Table 3.

TABLE 3

| Tested Agent | Dilution | Active ingredient (%) | Proportion of lesion (%) |
| --- | --- | --- | --- |
| Example 2 | × 2000 | 0.0055 | 19.8 |
| Comparative Example 1 | × 500 | 0.0045 | 45.6 |
| Comparative Example 2 | × 500 | 0.025 | 58.9 |
| No treatment |  |  | 88.5 |

The results of Table 3 indicate that the proportion of lesion of large patch of turfgrass observed when the polyoxin dry flowable of Example 2 was applied was lower than those observed when the polyoxin wettable powder of Comparative Example 1 and the pencycuron wettable powder of Comparative Example 3 were applied. In particular, the polyoxin dry flowable of Example 2 exhibited distinctly higher activity compared with the polyoxin wettable powder of Comparative Example 1.

TEST EXAMPLE 7
Effect for Rhizoctonia patch (spring deadspot) of turfgrass

Comparative test of effect against Rhizoctonia patch (Haruhage-sho) of turfgrass was performed by using the polyoxin dry flowable of Example 2, and a tolclofos-methyl wettable powder (trade name: Grancer Wettable Powder, active ingredient: 75% of tolclofos-methyl, manufacturer: Sumitomo Chemical Co., Ltd., represented as "Comparative Example 4" hereinafter).

Each agent was diluted in the predetermined degree of dilution shown in Table 4, and applied by a engine driven sprayer in a predetermined amount to golf course fairway where Mascarene grass (*Zoysia tenuifolia* Willd.) and Japanese lawngrass (Noshiba) were mixed-planted, and Rhizoctonia patch was observed on many spots. The agent was applied twice on October 26 and November 9. The test was carried out in a plot of 50 m$^2$ for each test in duplicate. On April 12 of the next year, proportion of lesion was determined for each plot. The results are shown in Table 4. Phytotoxicity was not seen in any plot when observed with the naked eye.

TABLE 4

| Tested Agent | Dilution | Active ingredient (%) | Applied amount (liter/m$^2$) | Proportion of lesion (%) | Protective value |
| --- | --- | --- | --- | --- | --- |
| Example 2 | × 1000 | 0.011 | 0.5 | 1.0 | 97.3 |
| Comparative Example 4 | × 1000 | 0.075 | 1.0 | 1.0 | 97.3 |
| No treatment |  |  |  | 37.5 |  |

Protective value = (1-Proportion of lesion of test plot/Proportion of lesion of non-treated plot) × 100

The results of Table 4 indicate that the polyoxin dry flowable of Example 2 exhibited comparable high activity against Rhizoctonia patch with a smaller amount compared with the tolclofos-methyl wettable powder of Comparative Example 4.

TEST EXAMPLE 8
Effect for Curvularia leaf blight

Comparative test of effect against Curvularia leaf blight of turfgrass was performed by using the polyoxin dry flowable of Example 2, and a thiram/TPN wettable powder (trade name: Dacogreen Wettable Powder, active ingredient: 50% of TPN and 30% of thiram, manufacturer: SDS Biotech K.K., represented as "Comparative Example 5" hereinafter).

Each agent was diluted in the predetermined degree of dilution shown in Table 5, and applied in a predetermined amount on May 26 to Mascarene grass which began to develop Curvularia leaf blight from late in May. The test was carried out in a plot of 2 m² for each test in triplicate. On June 5, proportion of disease was determined for each plot. The results are shown in Table 5. Phytotoxicity was not seen in any plot when observed with the naked eye.

TABLE 5

| Tested Agent | Dilution | Active ingredient (%) | Applied amount (liter/m²) | Proportion of disease (%) | Protective value |
|---|---|---|---|---|---|
| Example 2 | × 1000 | 0.0110 | 0.5 | 2.7 | 78.1 |
|  | × 2000 | 0.0055 | 1.0 | 3.4 | 72.4 |
| Comparative Example 5 | × 500 | TNP 0.05 Thiram 0.03 | 1.0 | 3.5 | 71.6 |
| No treatment |  |  |  | 12.3 |  |

Protective value = (1-Proportion of disease of test plot/Proportion of disease of non-treated plot) × 100

The results of Table 5 indicate that a higher protective value for Curvularia leaf blight of turfgrass was obtained when the polyoxin dry flowable of Example 2 was applied compared with when the thiram/TPN wettable ponder of Comparative Example 5 was applied.

TEST EXAMPLE 9
Effect for Rhizoctonia patch (Zou-no-ashiato)

Comparative test of effect against Rhizoctonia patch (Zou-no-ashiato) was performed by using the polyoxin dry flowable of Example 2, and the commercially available tolclofos-methyl wettable powder of Comparative Example 4.

Each agent was diluted in the predetermined degree of dilution shown in Table 6, and applied in a predetermined amount on October 2 by a engine driven sprayer to Japanese lawngrass of golf course rough which had begun to develop Rhizoctonia patch early in September. The test was carried out in a plot of 100 m² for each test, and proportion of lesion was determined for each plot on October 28. The results are shown in Table 6. Phytotoxicity was not seen in any plot when observed with the naked eye.

TABLE 6

| Tested Agent | Dilution (time) | Active ingredient (%) | Applied amount (liter/m²) | Proportion of lesion (%) | Protective value |
|---|---|---|---|---|---|
| Example 2 | × 1000 | 0.0110 | 0.5 | 0 | 100 |
|  | × 2000 | 0.0055 | 1.0 | 0 | 100 |
| Comparative Example 4 | × 1000 | 0.0750 | 1.0 | 0 | 100 |
| No treatment |  |  |  | 11.7 |  |

Protective value = (1-Proportion of lesion of test plot/Proportion of lesion of non-treated plot) × 100

The results of Table 6 indicate that the polyoxin dry flowable of Example 2 exhibits comparative high effect against Rhizoctonia patch with a smaller amount compared with the tolclofos-methyl wettable powder of Comparative Example 4.

TEST EXAMPLE 10
Effect for powdery mildew of rose plant

Comparative test of effect against powdery mildew of rose plant was performed by using the polyoxin dry flowable of Example 2, and the commercially available polyoxin dry flowable of Comparative Example 1.

Each agent was diluted in the predetermined degree of dilution as shown in Table 7, and applied in an amount of 500 ml to a rose plant infected by powdery mildew (variety: Paul's Pink, cultivated in a Wagner pot). The application was performed four times in total on September 19, September 26, October 3 and October 9. The test was carried out with one plant body for each test, and each plant was examined on October 16. Disease severity was calculated according to the following equation using a disease area of 30 leaves for each test, and protective value was calculated from the obtained value. The results are shown in Table 7.

Disease severity=[Σ(index number×number of corresponding leaves)/4×number of examined leaves]×100

Index number

| 0: Proportion of disease | 0% |
| 1: Proportion of disease | up to 10% |
| 2: Proportion of disease | up to 25% |
| 3: Proportion of disease | up to 50% |
| 4: Proportion of disease | higher than 50% |

Protective value=(1−Disease severity of treated plant/Disease severity of non-treated plant)×100

TABLE 7

| Tested agent | Concentration (ppm) | Protective value | Disease severity |
|---|---|---|---|
| Example 2 | 10 | 42.2 | 50.0 |
|  | 20 | 90.3 | 9.2 |
|  | 40 | 92.4 | 7.5 |
| Compartive Example 1 | 25 | 30.6 | 60.0 |
|  | 50 | 61.0 | 36.7 |
|  | 100 | 88.3 | 11.7 |
| No treatment |  |  | 86.9 |

The results of Table 7 indicate that the polyoxin dry flowable of Example 2 exhibits a higher protective value for powdery mildew of rose plant compared with the wettable powder of Comparative Example 1. While a little taint was observed on the leaves applied with the wettable powder of Comparative Example 1, no taint was observed applied with the dry flowable of Example 2.

What is claimed is:

1. A dry flowable composition containing a polyoxin compound, a surfactant and a water-soluble inorganic material selected from the group consisting of sodium sulfate, ammonium sulfate and mixtures thereof.

2. The dry flowable composition of claim 1 which contains one more polyoxin compounds produced by *Streptomyces cacaoi* var. asoensis.

3. The dry flowable composition of claim 1 which contains as the polyoxin compound one or more compounds selected from the group consisting of polyoxin A, polyoxin B, polyoxin D, polyoxin E, polyoxin F, polyoxin G, polyoxin H, polyoxin J, polyoxin K, polyoxin L, polyoxin M, polyoxin N, polyoxin O and salts thereof.

4. The dry flowable composition of claim 3 which contains as the polyoxin compound one or more compounds selected from the group consisting of polyoxin B, polyoxin D, and salts thereof.

5. The dry flowable composition of claim 4 wherein the salts are zinc salts, iron salts or titanium salts.

6. The dry flowable composition of claim 4 which contains zinc salt of polyoxin D as the polyoxin compounds.

7. The dry flowable composition of claim 1 which contains 5–30% by weight of the polyoxin compound.

8. The dry flowable composition of claim 1 which contains an anionic surfactant, or a nonionic surfactant, or both as the surfactant.

9. The dry flowable composition of claim 8 which contains an anionic surfactant and a nonionic surfactant as the surfactant.

10. The dry flowable composition of claim 8 which contains a formalin condensate of sodium naphthalenesulfonate as the anionic surfactant.

11. The dry flowable composition of claim 8 which contains a polyoxyethylene alkyl ether as the nonionic surfactant.

12. The dry flowable composition of claim 1 which has a particle size within the range of 90–500 $\mu$m.

13. The dry flowable composition of claim 1 which has a particle size within the range of 90–355 $\mu$m.

14. A method of preventing or treating large patch, brown patch, Rhizoctonia patch, Helminthosporium leaf blight, Curvularia leaf blight, or fairy rings in turf grass, which comprises applying to susceptible or effected turf grass an effective amount of the dry flowable composition of claim 1.

15. The method of claim 14 which the dry flowable composition applied to effected turf grass at an early stage of infection of, or before dormant period of large patch, brown patch, Rhizoctonia patch, Helminthosporium leaf blight, Curvularia leaf flight, or fairy rings.

16. A method of preventing or treating powdery mildew of rose plants which comprises applying to susceptible or effected rose plants an effective amount of the dry flowable composition of claim 1.

* * * * *